(12) United States Patent
Liu et al.

(10) Patent No.: US 11,884,636 B2
(45) Date of Patent: Jan. 30, 2024

(54) GONADOTROPIN RELEASING HORMONE RECEPTOR ANTAGONIST AND USE THEREOF

(71) Applicant: SHIJIAZHUANG YILING PHARMACEUTICAL CO., LTD., Hebei (CN)

(72) Inventors: Guoqiang Liu, Shanghai (CN); Wei Liu, Shanghai (CN); Yandong Wang, Shanghai (CN)

(73) Assignee: SHIJIAZHUANG YILING PHARMACEUTICAL CO., LTD., Shijiazhuang Hebei Province (CN)

( * ) Notice: Subject to any disclaimer, the term of this patent is extended or adjusted under 35 U.S.C. 154(b) by 0 days.

(21) Appl. No.: 17/920,029

(22) PCT Filed: May 20, 2021

(86) PCT No.: PCT/CN2021/094748
§ 371 (c)(1),
(2) Date: Oct. 20, 2022

(87) PCT Pub. No.: WO2021/213538
PCT Pub. Date: Oct. 28, 2021

(65) Prior Publication Data
US 2023/0144828 A1  May 11, 2023

(30) Foreign Application Priority Data

Apr. 20, 2020 (CN) .......................... 202010311436.8

(51) Int. Cl.
| | | |
|---|---|---|
| C07D 239/54 | (2006.01) |
| A61P 5/26 | (2006.01) |
| A61K 31/513 | (2006.01) |
| A61P 5/02 | (2006.01) |
| A61P 5/24 | (2006.01) |
| A61P 15/08 | (2006.01) |

(52) U.S. Cl.
CPC .......... *C07D 239/54* (2013.01); *A61K 31/513* (2013.01); *A61P 5/02* (2018.01); *A61P 5/24* (2018.01); *A61P 5/26* (2018.01); *A61P 15/08* (2018.01)

(58) Field of Classification Search
CPC .......... A61K 31/513; A61P 15/08; A61P 5/02; A61P 5/24; A61P 5/26; C07D 239/54
See application file for complete search history.

(56) References Cited

U.S. PATENT DOCUMENTS

2004/0048884 A1*  3/2004  Zhu ..................... A61P 13/08
                                                544/320
2013/0137661 A1*  5/2013  Kim ..................... A61P 43/00
                                                544/243

FOREIGN PATENT DOCUMENTS

| CN | 1819829 A | 8/2006 |
| WO | 2018189212 A1 | 10/2018 |
| WO | 2018224063 A2 | 12/2018 |

OTHER PUBLICATIONS

Shebley. Mohamad et al. ""Clinical Pharmacology of Elagolix: An Oral Gonadotropin Releasing Hormone Receptor Antagonist for Endometriosis"" x'Clinical Pharmacokinetics}, vol. 59. Nov. 21, 2019 (Nov. 21, 2019). p. 299.

Ng. Juki et al. ""Elagolix Pharmacokinetic Profiles in Women With Renal or Hepatic I7cairment"" xClinical Pharmacology in Drug DevelopmenJ, vol. 8. No. 8. Dec. 31, 2019 (Dec. 31, 2019). p. 1056 to p. 1058. tables 1-4.

Chen. Chen et al. ""Discovery of Sodium R-(+) 4-(2-5-(2-Fluoro-3-methoxyphenyl)-3-(2-fluoro-6-[ trifluoromethyl]-benzyl)-4-methyl-2. 6-dioxo-3. 6-dihydro-2H-pyrimidin-l-yl]-1-phenylethylamino} butyrate (Elagolix). a Potent and Orally Available Nonpeptide Antagonist of the Human Gonadotropin-Releasing Hormone Receptor"" Journal of Medicinal Chemistry, vol. 51. No. 23. Nov. 12, 2008 (Nov. 12, 2008).

* cited by examiner

*Primary Examiner* — Theodore R. Howell
(74) *Attorney, Agent, or Firm* — Global IP Services; Tianhua Gu

(57) ABSTRACT

The present invention provides a compound or a pharmaceutically acceptable salt, isomer, prodrug, polymorph or solvate thereof, and a preparation method therefor and use thereof. The compound provided in the present invention has comparable or superior activity to Elagolix as a GnRHR antagonist in calcium flux assays and have better pharmacokinetic properties.

9 Claims, 2 Drawing Sheets

GONADOTROPIN RELEASING HORMONE RECEPTOR ANTAGONIST AND USE THEREOF

CROSS REFERENCE TO RELATED PATENT APPLICATION

The present application is the US national stage of PCT/CN2021/094748 filed on 2021 May 20, which claims the priority of the Chinese patent application No. 202010311436.8 filed on 2020 Apr. 20, which application is incorporated herein by reference.

FIELD OF TECHNOLOGY

The present invention relates to the field of organic chemistry, in particular to a compound or a pharmaceutically acceptable salt, isomer, prodrug, polymorph or solvate thereof and to a preparation method therefor and use thereof.

BACKGROUND

Gonadotropin-releasing hormone (GnRH), also known as luteinizing hormone-releasing hormone (LHRH), is a decapeptide secreted by the hypothalamus. GnRH exerts its biological effects by binding to its GnRH receptor located in the anterior pituitary gland, which can stimulate the biosynthesis and secretion of luteinizing hormone (LH) and follicle stimulating hormone (FSH). The LH and FSH act synergistically to stimulate the development of germ cells in the ovary or testis and the production and secretion of gonadal hormones.

Therapeutic agents targeting the GnRH receptor can inhibit hypothalamic-pituitary-gonadal axis function and have been widely used for treating gonadal hormone-dependent diseases such as prostate cancer, breast cancer, endometriosis, hysteromyoma, benign prostate hypertrophy, assisted reproductive treatments, and precocious puberty.

The therapeutic agents currently used are GnRH receptor agonists or antagonists. The GnRH receptor agonists have been approved for the treatment of reproductive hormone-dependent diseases such as prostate cancer, premenopausal breast cancer, endometriosis, and uterine fibrosis. At the beginning of treatment, the GnRH receptor agonists can stimulate the pituitary gonadotropic cells, increase the secretion of gonadotropins and cause a "flare up" effect that lasts about 1 to 3 weeks. In contrast, long-term administration can deplete gonadotropins and subsequently downregulates this receptor, leading after a period of time to suppression of gonadotropins and downregulation of circulating gonadotropins such as estrogen, progesterone and testosterone, thus exerting a therapeutic effect on hormone-dependent diseases.

In contrast to GnRH receptor agonists, GnRH receptor antagonists inhibit the pituitary-gonadal axis directly and rapidly by competitively binding to pituitary GnRH receptors, inhibiting the endogenous luteinizing hormone peak and reducing estrogen levels. GnRH receptor antagonists have a rapid onset of action without any agonistic action and do not cause a "flare up" effect, and the pituitary function can be restored 2-4 d after discontinuation. Adverse reactions of GnRH receptor agonists due to the "flare up" effect at the beginning of treatment can be avoided. Moreover, the medication time can be shortened clinically, which is more economical and convenient.

Several peptide GnRH receptor antagonists are currently approved for marketing for assisting reproduction in infertility and for the treatment of advanced prostate cancer. However, these peptide GnRH analogs require being administered through subcutaneous injection or intranasal spray, or injection of long-acting reservoirs, cannot be administered orally, and have disadvantages such as stimulation of histamine release response at the injection site and slow clearance after cessation of administration, which limit their application. In contrast, non-peptide GnRH receptor antagonists can avoid pains caused by injection and allergic reactions due to histamine release, and can be administered orally to improve patient compliance, thus having more advantages (Sarma, PKS et al, Expert Opinion on Therapeutic Patents 16(6):733-751, 2006).

Elagolix is the first oral non-peptide GnRH receptor antagonist marketed for the treatment of endometriosis and is also being investigated for other estrogen-dependent diseases such as hysteromyoma. Elagolix belongs to the pyrimidine-2,4-diketone compounds (Guo et al., CN200480019502.3) and blocks the GnRH signal channel by competitively binding to GnRH receptors in the pituitary, reversibly reducing the secretion of ovarian gonadal hormones, estradiol and progesterone.

Although Elagolix is orally absorbable, it has only low to moderate cellular permeability and low oral bioavailability, with absolute oral bioavailability of only 10%, 5.8% and 11% in mice, rats and monkeys, respectively (Chen, et al. Discovery of Sodium R-(+)-4-{2-[5-(2-Fluoro-3-methoxyphenyl)-3-(2-fluoro-6-[trifluoromethyl]-benzyl)-4-methyl-2,6-dioxo-3,6-dihydro-2H-pyrimidin-1-yl]-1-phenylethylamino}butyrate (Elagolix), a Potent and Orally Available Nonpeptide Antagonist of the Human Gonadotropin-Releasing Hormone Receptor, J. Med. Chem. 2008, 51, 7478-7485). However, rats given orally using radiolabeled Elagolix excrete nearly 50% of the total radioactivity through the bile, indicating that Elagolix may have a hepatic first-pass effect and that most of the drug fails to enter into the circulation to exert its effect. This results in a higher clinical treatment dose (the recommended clinical dose of Elagolix is 150 mg, qd or 200 mg, bid). Moreover, the total radioactivity in rats after oral administration is mainly confined to the gastrointestinal tract and the liver. Elagolix also shows a high apparent volume of distribution (1674 L) in human bodies, both indicating a high tissue distribution profile. Excessive hepatic distribution can lead to a risk of Elagolix hepatotoxicity (elevated hepatic transaminases) and effects on hepatic drug enzymes (Elagolix is a substrate for CYP3A, P-gp and OATP1B1, and an inhibitor of P-gp with weak to moderate induction of P450 (CYP) 3A) (FDA, Orilissa (elagolix), 210450Orig1s000MultiD, 2018).

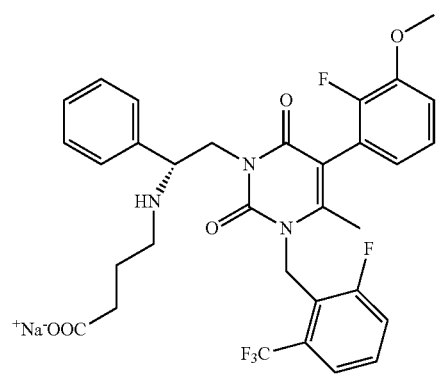

Elagolix

Although meaningful research has been conducted in this field, there is still a need for effective small molecule GnRH receptor antagonists with more desirable pharmacological properties. There is also a need for pharmaceutical compositions containing this GnRH receptor antagonist, and methods of using it to treat disease states such as those related to gonadal hormones.

SUMMARY

The present invention provides a compound or a pharmaceutically acceptable salt, isomer, prodrug, polymorph or solvate thereof, and a preparation method therefor and use thereof.

Provided in one aspect of the present invention is a compound or a pharmaceutically acceptable salt, isomer, prodrug, polymorph or solvate thereof. The chemical structural formula of the compound is shown in Formula I:

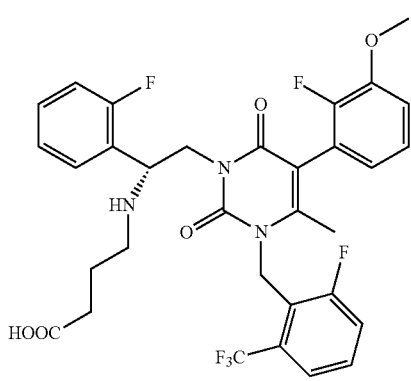 [SMILES: COc1cccc(-c2c(C)n(Cc3c(F)cccc3C(F)(F)F)c(=O)n(C[C@H](NCCCC(=O)O)c3ccccc3F)c2=O)c1F]

I

In some embodiments of the present invention, the isomer is selected from the group consisting of an enantiomer, a diastereoisomer, a cis-trans isomer and a stereoisomer.

Provided in another aspect of the present invention is a preparation method for the above compound, comprising: hydrolyzing a compound of Formula 1-12 to prepare and obtain the compound of Formula I, with the following reaction equation.

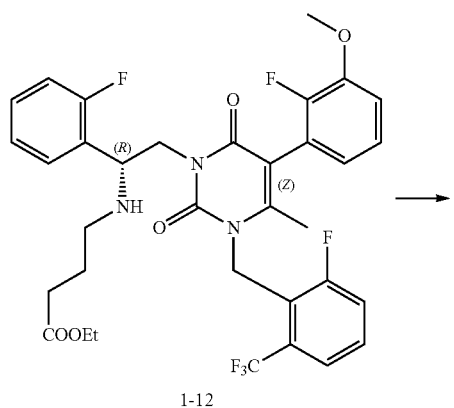

1-12

→

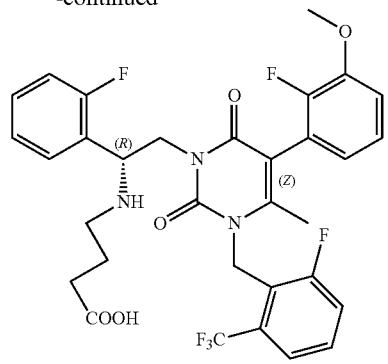

In some embodiments of the present invention, the hydrolysis reaction can usually be carried out in the presence of a base.

Provided in another aspect of the present invention is a use of the compound or the pharmaceutically acceptable salt, isomer, prodrug, polymorph or solvate thereof in preparing a drug.

In some embodiments of the present invention, the drug is a gonadotropin-releasing hormone receptor antagonist.

In some embodiments of the present invention, the drug is a drug for treating a gonadal hormone-related disease.

In some embodiments of the present invention, the gonadal hormone-related diseases is selected from the group consisting of endometriosis, amenorrhea, menstrual irregularity, hysteromyoma, metrofibroma, polycystic ovarian disease, endometriosis, uterine leiomyoma, lupus erythematosus, hirsutism, precocious puberty, dwarfism, acne, alopecia, gonadotropin-dependent tumor, gonadotropin-producing pituitary adenomas, sleep apnea, irritable bowel syndrome, premenstrual syndrome, benign prostatic hyperplasia, contraception and infertility, and Alzheimer's disease.

In some embodiments of the present invention, the gonadotropin-dependent tumor is selected from prostate cancer, uterine cancer, breast cancer, ovarian cancer, and pituitary gonadotropic adenomas.

Provided in another aspect of the present invention is a drug composition, comprising the above compound or the pharmaceutically acceptable salt, isomer, prodrug, polymorph or solvate thereof.

DETAILED DESCRIPTION

Figure 1:
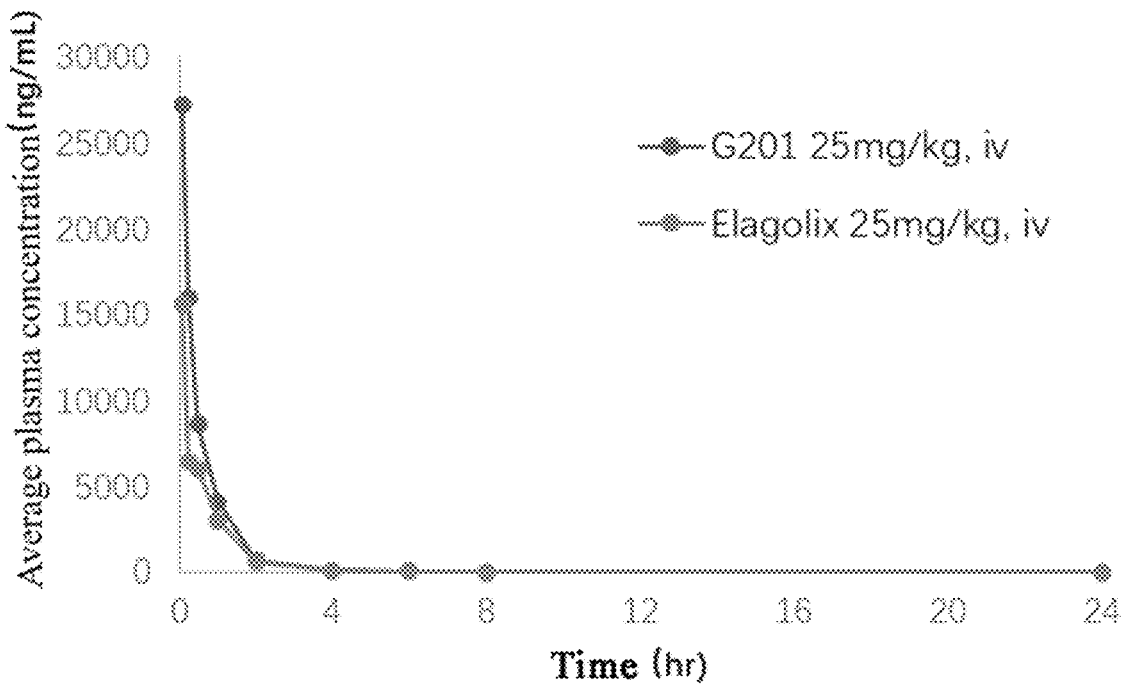
FIG. 1 shows a plasma concentration-time curve diagram of G201/Elagolix intravenously injected to SD rats in Example 3 of the present invention.

In order to make the inventive purpose, technical solutions and beneficial technical effects of the present invention clearer, the following is a further detailed description of the present invention in combination with examples, and those skilled in the art can easily understand other advantages and efficacy of the present invention from the contents disclosed in the specification.

Upon extensive practical research, the inventors of the present invention accidentally discovered a new kind of fluoro-substituted pyrimidinedione compound through structural modification of Elagolix. The compound has better biological activity and more desirable pharmacokinetic properties than traditional Elagolix, etc., thus providing a new compound that can be used as a gonadotropin-releasing hormone (GnRH) receptor antagonist, on the basis of which the present invention was completed.

Provided in the first aspect of the present invention is a compound or a pharmaceutically acceptable salt, isomer, prodrug, polymorph or solvate thereof. The chemical structural formula of the compound is shown in Formula I:

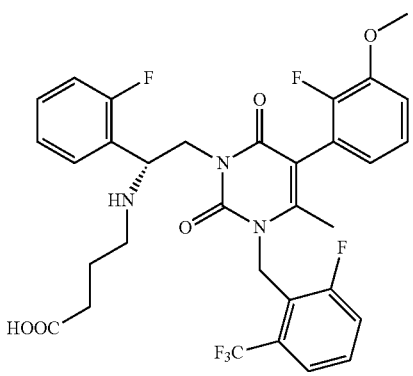

In the present invention, the term "salt" should be understood to mean any form of an active compound used in the present invention. The compound can be in an ionic form or charged or coupled to a counter ion (cation or anion) or in a solution. This definition can also include a quaternary ammonium salt and complex of active molecules with other molecule and ion, especially the complex formed through an ionic interaction. This definition particularly includes a physiologically acceptable salt, a term that can be understood as equivalent to "pharmacologically acceptable salts".

In the present invention, the term "pharmaceutically acceptable salt" generally refers to any salt that is physiologically tolerable (which generally means that it is nontoxic, especially as a result of the counter ion) when used therapeutically in an appropriate manner (especially when applied or used in human and/or mammal). The physiologically acceptable salt can be formed with a cation or base. In the context of the present invention, particularly when administered in human and/or mammal, the physiologically acceptable salt should be understood as a salt formed from at least one compound provided in accordance with the present invention, usually an acid (deprotonated), for example, the physiologically acceptable salt can be a salt formed from an anion and at least one physiologically tolerable cation (preferably an inorganic cation). In the context of the present invention, the physiologically acceptable salt can specifically include a salt formed with an alkali and an alkaline earth metal, and a salt formed with an ammonium cation ($NH_4^+$), and can specifically include, but are not limited to, a salt formed with (mono-) or (di-) sodium, (mono-) or (di-) potassium, magnesium or calcium.

The physiologically acceptable salt can also be formed with an anion or acid, and in the context of the present invention, especially when administered in human and/or mammal, the physiologically acceptable salt should be understood as a salt formed from at least one compound provided in accordance with the present invention, usually protonated (e.g. on nitrogen), for example, the physiologically acceptable salt can be a salt formed from a cation and at least one physiologically tolerable anion. In the context of the present invention, the physiologically acceptable salt can specifically include a salt formed from a physiologically tolerable acid, i.e., a salt formed from a specific active compound and a physiologically tolerable organic or inorganic acid, which can specifically include, but are not limited to, hydrochloric acid, hydrobromic acid, sulfuric acid, methanesulfonic acid, formic acid, acetic acid, oxalic acid, succinic acid, malic acid, tartaric acid, mandelic acid, fumaric acid, lactic acid, or citric acid. An exemplary pharmaceutically acceptable salt of the compound of Formula I has the following chemical structural formula:

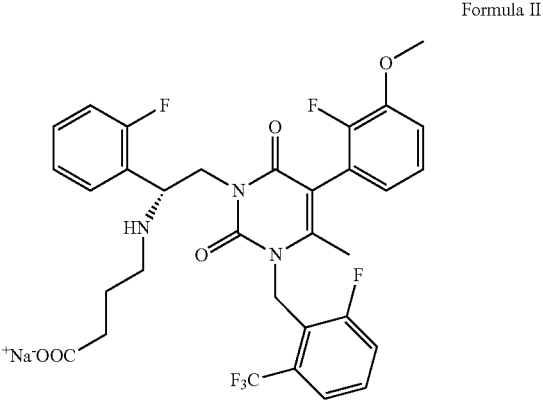

Formula II

The compound of the present invention represented by Formula I above can include an enantiomer depending on the chiral center present or an isomer depending on the double bond present (e.g. Z, E). A single isomer, enantiomer, diastereoisomer or cis-trans isomer and mixture thereof all fall within the scope of the present invention.

The term "prodrug" in the present invention is used in its broadest sense and includes those derivatives that can be converted in vivo to the compound of the present invention. Methods for preparing a prodrug of the specified acting compound should be known to those skilled in the art, referring to, for example, the relevant disclosure in, e.g., Krogsgaard-Larsen et al, "Textbook of Drug design and Discovery" Taylor & Francis (April 2002).

In the present invention, the term "solvate" generally refers to any form of a substance obtained by combining the active compound according to the invention with another molecule (usually a polar solvent) through a non-covalent bond, which can specifically include, but is not limited to, hydrates and alcohols, such as methanolates.

Provided in the second aspect of the present invention is a preparation method for the compound provided in the first aspect of the present invention, including: hydrolyzing a compound of Formula 1-12 to prepare and obtain the compound of Formula I, with the following reaction equation:

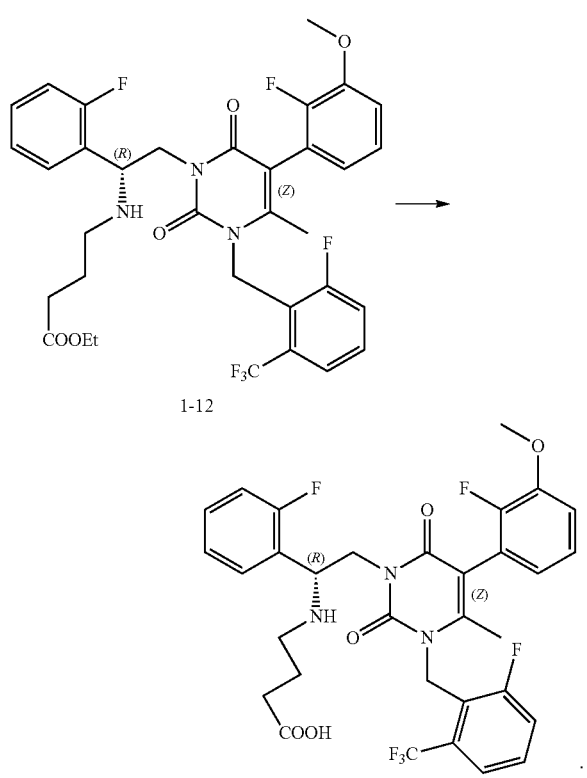

1-12

In the preparation method provided in the present invention, the hydrolysis reaction can usually be carried out in the presence of a base. Those skilled in the art can select and use a suitable type and usage amount of base for the above hydrolysis reaction. For example, the base can be a hydroxide of an alkali metal, etc., and more specifically, can be lithium hydroxide, etc. In another example, the usage amount of the base is usually substantially equal or excessive with respect to the compound of Formula 1-12, specifically, the molar ratio of the compound of Formula 1-12 to the base can be 1:1.4 to 1.6.

In the preparation method provided in the present invention, the hydrolysis reaction can usually be carried out from room temperature to the boiling point of the reaction solvent, and preferably can be carried out at room temperature. Those skilled in the art can adjust the reaction time of the hydrolysis reaction appropriately according to the reaction process. The method for monitoring the reaction process should be known to those skilled in the art, for example, it can be chromatography, nuclear magnetic resonance and other analytical methods, and the specific reaction time can be, for example, 0.5 to 1 hour, 1 to 1.5 hours, 1.5 to 2 hours, 2 to 3 hours, 3 to 4 hours or longer.

In the preparation method provided in the present invention, the hydrolysis reaction is usually carried out in the presence of a solvent, which can usually be a good solvent for the reaction material and needs to contain water, so that the reaction material can be adequately dispersed and the reaction can proceed smoothly. The type and usage amount of a suitable reaction solvent should be known to those skilled in the art. For example, the reaction solvent can contain water and can also contain ether solvents, etc., specifically tetrahydrofuran, etc.

In the preparation method provided in the present invention, those skilled in the art can select a suitable method for post-treatment of a reaction product, which can include, for example, high-performance chromatographic preparation, and lyophilization.

Provided in the third aspect of the present invention is a use of the compound provided in the first aspect or the pharmaceutically acceptable salt, isomer, prodrug, polymorph or solvate thereof for preparing a drug. The compound of the present invention can effectively inhibit the GnRH receptor and thus can act as a gonadotropin-releasing hormone receptor antagonist and can further be used for the treatment of a gonadal hormone-related disease. The gonadotropin-releasing hormone receptor antagonist provided in the present invention can be applied to a wide range of therapeutic use and can be used for treating various gonadal hormone-related disease conditions in males and females, as well as in mammals in general (also referred to as "individuals" in the present invention). The gonadal hormone-related disease can specifically be, for example, endometriosis, amenorrhea, menstrual irregularit, hysteromyoma, metrofibroma, polycystic ovarian disease, endometriosis, uterine leiomyoma, lupus erythematosus, hirsutism, precocious puberty, dwarfism, acne, alopecia, gonadotropin-dependent tumor (e.g., prostate cancer, uterine cancer, breast cancer, ovarian cancer, and pituitary gonadotropic adenomas), gonadotropin-producing pituitary adenomas, sleep apnea, irritable bowel syndrome, premenstrual syndrome, benign prostatic hyperplasia, contraception and infertility, and Alzheimer's disease.

Provided in the fourth aspect of the present invention is a drug composition, including the compound provided in the first aspect or the pharmaceutically acceptable salt, isomer, prodrug, polymorph or solvate thereof, and also including at least one pharmaceutically acceptable carrier.

In the present invention, the composition can include one or more pharmaceutically acceptable carriers for the administration of therapeutic agents, the carriers do not themselves induce the production of antibodies harmful to the individual receiving the composition and are not excessively toxic after administration. These carriers are well known to those skilled in the art, for example, as disclosed in Remington's Pharmaceutical Sciences (Mack Pub. Co., N. J. 1991) with respect to pharmaceutically acceptable carriers. Specifically, the carrier can include, but is not limited to, one or more of saline, a buffer solution, glucose, water, glycerol, ethanol, adjuvant, etc.

In the drug composition provided in the present invention, the compound can act as a single active component, or can be combined with other active components to form a combined preparation. Said other active components can be various other drugs that can be used for treating gonadal hormone-related diseases. The content of the active components in the composition is usually a safe and effective amount, and the safe and effective amount should be adjustable for those skilled in the art. For example, the application amount of the compound and the active component in the drug composition usually depends on the weight of a patient, the mode of administration, the condition and severity of the disease. For example, the application amount of the compound that acts as an active ingredient can usually be 0.1 to 10 mg/kg/day, 0.1 to 0.5 mg/kg/day, 0.5 to 1 mg/kg/day, 1 to 2 mg/kg/day, 2 to 3 mg/kg/day, 3 to 4 mg/kg/day, 4 to 5 mg/kg/day, 5 to 6 mg/kg/day, 6 to 8 mg/kg/day, 8 to 10 mg/kg/day, more preferably 0.5 to 5 mg/kg/day.

The compound provided in the present invention is applicable to any form of administration, either orally or parenterally, for example, by pulmonary, transnasal, transrectal and/or intravenous injection, and more specifically by intradermal, subcutaneous, intramuscular, intra-articular, intraperitoneal, pulmonary, buccal, sublingual, transnasal, transdermal, vaginal, oral or parenteral administration. Those skilled in the art can select a suitable formulation form depending on the mode of administration, for example, a formulation form suitable for oral administration can include, but is not limited to, pills, tablets, chewables, capsules, granules, drops, or syrups, etc., and then, for example, a formulation form suitable for parenteral administration can include, but is not limited to, solutions, suspensions, rehydratable dry formulations, or sprays, etc., and in another example, a formulation form suitable for rectal administration can usually be suppositories.

Provided in the fifth aspect of the present invention is a therapeutic method, including: administering to an individual a therapeutically effective amount of the compound provided in the first aspect of the present invention, or the drug composition provided in the fourth aspect of the present invention.

In the present invention, the term "individual" generally includes a human, and a non-human primate such as a mammal, dog, cat, horse, sheep, pig, cow, etc., who can benefit from treatment with the preparation, kit or combined preparation.

In the present invention, the term "therapeutically effective amount" generally refers to an amount that, after an appropriate period of administration, is capable of achieving the effect of treating a disease as listed above.

The compound provided in the present invention has comparable or superior activity to Elagolix as a GnRHR antagonist in calcium flux assays; in pharmacokinetic assays, the compound provided in the present invention has significantly higher absolute bioavailability than Elagolix; in plasma protein binding assays, the compound provided in the present invention has a slightly higher binding rate with SD rat plasma and healthy human plasma protein than Elagolix, and there is no drug concentration dependence in protein binding. As can be seen, the compound or the pharmaceutically acceptable salt, isomer, prodrug, polymorph or solvate thereof provided in the present application has better bioavailability and more desirable pharmacokinetic properties than other similar drugs in the prior art, and has a good industrial prospect.

The invention of the present application is further described below by way of examples, but the scope of the present application is not thereby limited.

Example 1

A compound G201 in the example has the following specific preparation route.

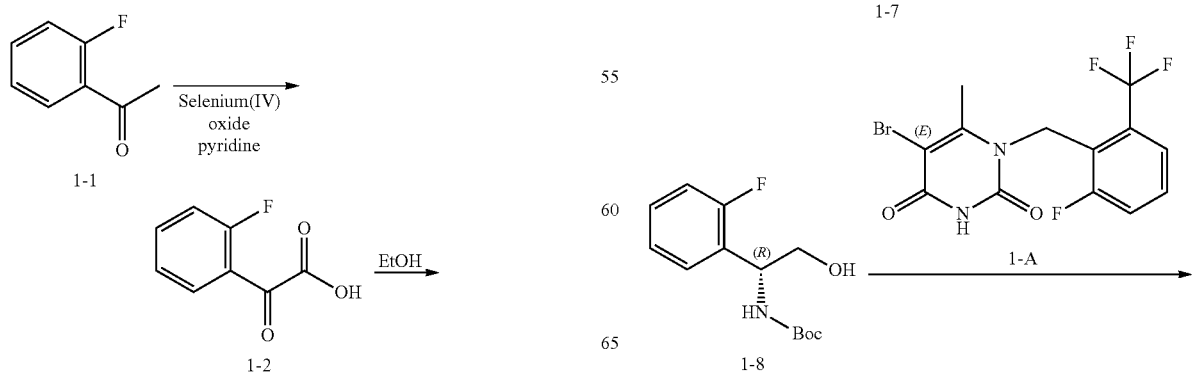

-continued

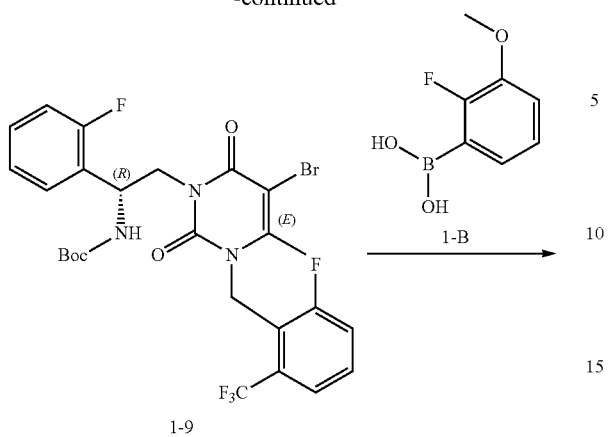

1-9

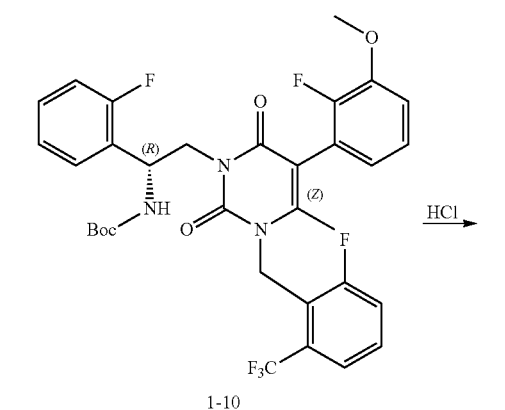

1-10

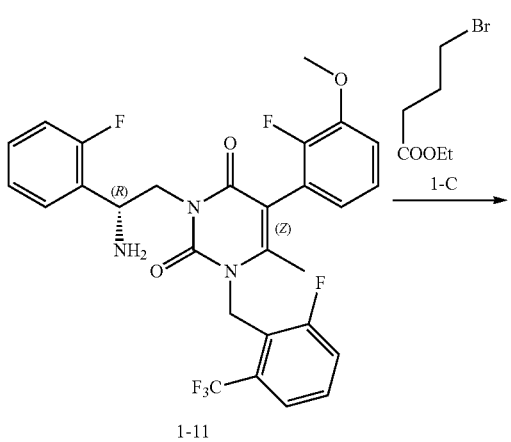

1-11

1-12

-continued

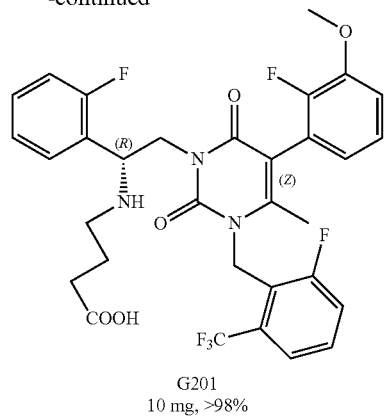

G201
10 mg, >98%

A compound 1-1 (10 g, 72.4 mmol), pyridine (200 mL) and selenium dioxide (16 g, 144.8 mmol) were added into a three-necked flask. The mixture reacted at 100° C. for 2 hours under nitrogen protection. After the completion of the reaction, suction filtration was carried out, a filtrate was spin-dried, 1 N of hydrochloric acid was added, and extraction was carried out using ethyl acetate. An organic phase was washed with a saturated salt solution, dried with anhydrous sodium sulfate, subjected to suction filtration and spin-dried to obtain an off-white solid 1-2 (12 g).

The compound 1-2 (12 g, 71.4 mmol) and methanol (200 mL) were added into a three-necked flask. Thionyl chloride (17 g, 142.8 mmol) was dropwise added at 0° C., and the mixture was stirred overnight at room temperature. After the completion of the reaction, the methanol was span-dried, a saturated aqueous sodium bicarbonate solution was added, and extraction was carried out using ethyl acetate. An organic phase was washed with a saturated salt solution, dried with anhydrous sodium sulfate, subjected to suction filtration and spin-dried to obtain a pale yellow oily substance 1-3 (9 g, 49.4 mmol).

The compound 1-3 (4 g, 20.4 mmol), anhydrous tetrahydrofuran (60 mL) and (R)-tert-butylsulfinamide (2.47 g, 20.4 mmol) were added into a three-necked flask. Tetraisopropyl titanate (11.6 g, 40.8 mmol) was added under nitrogen protection, and reflux stirring was carried out for 6 hours. After the completion of the reaction, water was added to quench the reaction, ethyl acetate was added for dilution, and suction filtration was carried out. A filtrate was separated, and an aqueous phase was extracted with ethyl acetate. An organic phase was combined and washed with a saturated salt solution, dried with anhydrous sodium sulfate, subjected to suction filtration and spin-dried to obtain a yellow oily substance 1-4 (6 g, 19.2 mmol).

The compound 1-4 (6 g, 19.2 mmol) and methanol (60 mL) were added into a three-necked flask. Sodium borohydride (1.1 g, 28.7 mmol) was added in batches at 0° C., and the mixture reacted at room temperature for 3 hours. After the completion of the reaction, water was added to quench the reaction, and extraction was carried out using ethyl acetate. An organic phase was washed with a saturated salt solution, dried with anhydrous sodium sulfate, subjected to suction filtration, spin-dried and purified by column chromatography (petroleum ether/ethyl acetate=10:1 to 5:1) to obtain a yellow oily substance 1-5 (3 g, 9.5 mmol).

The compound 1-5 (3 g, 9.5 mmol) and anhydrous tetrahydrofuran (40 mL) were added into a three-necked flask. Lithium aluminum hydride (0.43 g, 11.4 mmol) was added in batches at 0° C., and the mixture reacted at room temperature for 2 hours. After the completion of the reaction, water was added to quench the reaction, and extraction was carried out using ethyl acetate. An organic phase was washed with a saturated salt solution, dried with anhydrous sodium sulfate, subjected to suction filtration, spin-dried and purified by column chromatography (petroleum ether/ethyl acetate=10:1 to 3:1) to obtain a yellow oily substance 1-6 (1.5 g, 5.8 mmol).

The compound 1-6 (1.5 g, 5.8 mmol), ethyl acetate (10 mL) and hydrogen chloride/ethyl acetate (10 mL) were added into a single-necked flask. The mixture reacted at room temperature for 1 hour. After the completion of the reaction, the mixture was span-dried to obtain a yellow solid 1-7 (1.5 g), which was directly put into the next step.

The compound 1-7 (1.5 g), dichloromethane (20 mL), triethylamine (2.9 g, 28.9 mmol) and di-tert-butyl dicarbonate (1.5 g, 6.9 mmol) were added into a single-necked flask. The mixture reacted at room temperature for 16 hours. After the completion of the reaction, the mixture was span-dried and purified by column chromatography (petroleum ether/ethyl acetate=15:1 to 10:1) to obtain a yellow solid 1-8 (1.3 g, 5.1 mmol).

The compound 1-8 (1.3 g, 5.1 mmol), a compound 1-A (1.9 g, 5.1 mmol), triphenylphosphine (2.0 g, 7.6 mmol), anhydrous tetrahydrofuran (30 mL) and diethyl azodicarboxylate (1.5 g, 7.6 mmol) were added into a three-necked flask. A reflux reaction was carried out for 16 hours. After the completion of the reaction, the mixture was spin-dried and purified by column chromatography (petroleum ether/ethyl acetate=10:1 to 5:1) to obtain a white solid 1-9 (2.1 g, 3.4 mmol).

The compound 1-9 (2.1 g, 3.4 mmol), a compound 1-B (0.7 g, 4.1 mmol), sodium carbonate (1.4 g, 13.6 mmol), dioxane (27 mL), water (9 mL) and tetrakis(triphenylphosphine)palladium (0.4 g, 0.34 mmol) were added into a three-necked flask. The mixture reacted at 90° C. for 16 hours under nitrogen protection. After the completion of the reaction, suction filtration was carried out, and a filtrate was spin-dried and purified by column chromatography (petroleum ether/ethyl acetate=15:1 to 5:1) to obtain a pale yellow solid 1-10 (1.35 g, 2.0 mmol).

The compound 1-10 (250 mg, 0.38 mmol), dichloromethane (2 mL) and trifluoroacetic acid (2 mL) were added into a single-necked flask, and the mixture reacted at room temperature for 1 hour. After the completion of the reaction, the mixture was span-dried to obtain a yellow solid 1-11 (210 mg).

The crude compound 1-11 (210 mg), acetonitrile (3 mL), a compound 1-C (220 mg, 1.13 mmol) and potassium carbonate (156 mg, 1.13 mmol) were added into a single-necked flask, and the mixture reacted at 80° C. for 16 hours. After the completion of the reaction, the mixture was spin-dried, and by means of preparative thin layer chromatography (petroleum ether/ethyl acetate=1.5/1), a colorless oily substance 1-12 (210 mg, 0.31 mmol) was obtained.

The compound 1-12 (210 mg, 0.31 mmol), tetrahydrofuran (3 mL), water (2 mL) and lithium hydroxide (20 mg, 0.47 mmol) were added into a single-necked flask, and the mixture reacted at room temperature for 2 hours. After the completion of the reaction, the mixture was span-dried, high-pressure preparation was carried out (acetonitril 10 to 55/7 minutes), and freeze-drying was carried out to obtain a white solid G201 (20 mg). 1HNMR CD3OD δ: 7.62-7.64 (m, 1H), 7.39-7.57 (m, 4H), 7.11-7.23 (m, 4H), 6.65-6.80 (m, 1H), 5.38-5.49 (m, 2H), 4.81 (q, 1H), 4.46-4.53 (m, 2H), 3.90 (s, 3H), 2.81-2.84 (m, 2H), 2.37-2.40 (m, 2H), 2.12 (d, 3H), 1.79-1.83 (m, 2H). LC-MS: m/z=649.8(M+1), LCMS purity>98%.

Example 2

Calcium Flux Assay:

Intracellular calcium changes of cell line CHO-K1/GNRHR/Gα15 that is stable of a recombinant human gonadotropin-releasing hormone receptor (GnRHR) were measured using an FLIPR calcium flux assay kit (Calcium 4 assay kit). GnRHR is a G protein-coupled receptor (GPCRs), and a GPCRs signal enabled intracellular calcium release through a Gq pathway. Therefore, functional changes of GnRHR, which carried out signal transduction through the Gq pathway, can be detected by detecting intracellular calcium release with a calcium-sensitive fluorescent probe. The assay steps were as follows:

1. Cells were seeded in 384-well plates (Corning, Cat #:3764) at a density of 10,000 cells/well with an F12+10% FBS medium (20 µl/well) and cultured overnight (18 h).
2. A dye working solution was prepared from a probenecid stock solution (500 mM) and a Calcium 4 stock solution mixed at 1:100. A sample to be tested G201 and Elagolix (2 mM in DMSO) was diluted with an assay buffer, specifically, 5 µl of 2 mM stock solution was taken and diluted to 200 µl (50 µM) to obtain a 5× sample working solution of a first concentration. 20 µl of the 5× sample working solution was taken and diluted to 200 µl, and after even mixing, a sample working solution of a second concentration was obtained. A total of eight gradient dilutions of sample working solutions were prepared respectively. After adding 20 µl/well of the dye working solution and 10 µl/well of the sample working solution to the cells cultured overnight, the cells continued to be incubated in a cell incubator for 45 min and equilibrated away from light for 15 min at room temperature.
3. A 5X EC80 agonist working solution was prepared, specifically, 5 µl of 1 mM Buserelin stock solution was taken and diluted to 200 µl (25 µM), then 71 µl of 25 µM Buserelin working solution was taken and diluted to 10 ml (0.179 µM) with the assay buffer.
4. Corresponding to the location of the cells in the 384-well plate, the agonist working solution was added to the sample plate at 40 µl/well, and the FLIPR assay was carried out.

Test result: G201 can dose-dependently inhibit intracellular calcium release from CHO-K1/GNRHR/Gα15 cells with $EC_{50}$ of 37.59 nM, and $EC_{50}$ of Elagolix is 45.73 nM. It was shown that G201 was a GnRHR antagonist with comparable or superior activity to Elagolix.

Example 3

Rat Pharmacokinetic Assay:

12 female SD rats, divided into four groups of three per group, were administrated G201 (dissolved in saline containing 5% N,N-dimethylacetamide and 5% cremophor ELL) and Elagolix Sodium (dissolved directly in saline) intravenously and by gavage at doses of 25 mg/kg and 50 mg/kg, respectively. Food was fasted overnight before administration and resumed 4 h after administration, with free access to water throughout the assay period. Blood was collected from the retro-orbital venous plexus before and 5, 15, 30 min, 1, 2, 4, 6, 8, 24 h after administration, and the volume of blood collected was approximately 0.2 mL. A whole blood sample centrifuged at 4000 rpm for 10 min within 1 h from collection. The upper layer of plasma was separated and stored in a refrigerator at minus 20° C. within 1 h until analysis. After the plasma sample were precipitated by methanolic protein at 1:8, G201 and Elagolix plasma concentrations were measured by an LC-MS/MS method, and main pharmacokinetic parameters were calculated by applying DAS3.2.7 software.

The result showed that G201 intravenously administered had an average CL of 1.62 L/h/kg, an average $t_{1/2}$ of 0.79 h, and an average Vz of 1.82 L/kg. In contrast, an average CL and Vz of Elagolix Sodium were 2.48 L/h/kg and 8.46 L/kg, respectively. The apparent distribution volume of G201 was significantly lower than that of Elagolix, showing reduced tissue distribution.

Figure 2:
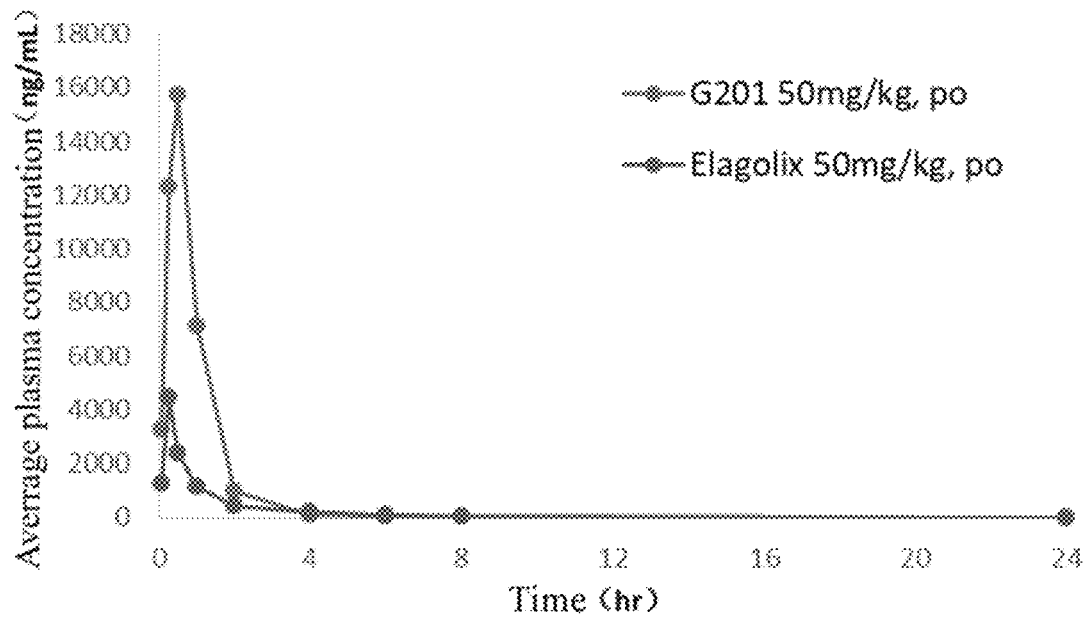
FIG. 2 shows a plasma concentration-time curve diagram of G201/Elagolix orally administered in SD rats in Example 3 of the present invention.

G201 was absorbed faster after oral administration to the rats, with $T_{max}$ of 0.42 h, and average $AUC_{0-\infty}$ of 16,351.7 h*ng/mL, which was three times of that of Elagolix Sodium. The absolute bioavailability of G201 orally administered was 51.92%, which was significantly higher than that of Elagolix Sodium (23.65%). The plasma concentration-time curve of G201/Elagolix intravenously administered was shown in FIG. 1, the plasma concentration-time curve for oral administration was shown in FIG. 2, and pharmacokinetic parameters were shown in Table 1.

TABLE 1 pharmacokinetic parameters of G201 and Elagolix in SD rats (mean value, n = 3)

| Parameter | Unit | Oral gavage (50 mg/kg) | | Intravenous injection (25 mg/kg) | |
|---|---|---|---|---|---|
| | | G201 | Elagolix Sodium | G201 | Elagolix Sodium |
| $AUC_{0-24\,h}$ | h*ng/mL | 16325.1 | 4829.3 | 15722.0 | 10207.8 |
| $AUC_{0-\infty}$ | h*ng/mL | 16351.7 | 4874.6 | 15740.9 | 10213.2 |
| $t_{1/2z}$ | h | 4.70 | 4.53 | 0.79 | 2.16 |
| $T_{max}$ | h | 0.42 | 0.42 | 0.08 | 0.08 |
| Vz | L/kg | — | — | 1.82 | 8.46 |
| CLz | L/h/kg | — | — | 1.62 | 2.48 |
| $C_{max}$ | ng/mL | 17009.2 | 4659.1 | 27201.7 | 15604.3 |
| F | % | 51.9 | 23.7 | — | — |

AUC: area under the plasma concentration-time curve;
$t^{1/2}z$: biological half-life;
$T_{max}$: time to peak;
Vz: apparent volume of distribution;
CLz: clearance rate;
$C_{max}$: peak plasma drug concentration; and
F: absolute bioavailability, the same below.

Example 4

Mouse Pharmacokinetic Assay:

10 female ICR mice, divided into two groups of five per group, were administrated G201 intravenously and by oral gavage, respectively, at a dose of 10 mg/kg. Blood was collected from the retro-orbital venous plexus 0.083, 0.25, 0.5, 1, 2, 4, 6, 8 h after administration, and the volume of blood collected was approximately 0.1 mL. A blood sample was centrifuged at 4000 rpm for 10 min within 1 h. The upper layer of plasma was separated and stored in a refrigerator at minus 80° C. within 1 h to be measured. The subject animals were fasted for at least 12 h before blood collection and were not water fasted. Food and water were fasted during blood collection and free 2 h after administration. The plasma concentration of G201 in the ICR mice was measured by an LC-MS/MS method, and main pharmacokinetic parameters were calculated by applying DAS 3.2.7 pharmacokinetic software and include $AUC_{0-4}$, $AUC_{0-\infty}$, $C_{max}$, $t_{1/2}$, etc.

Figure 3:
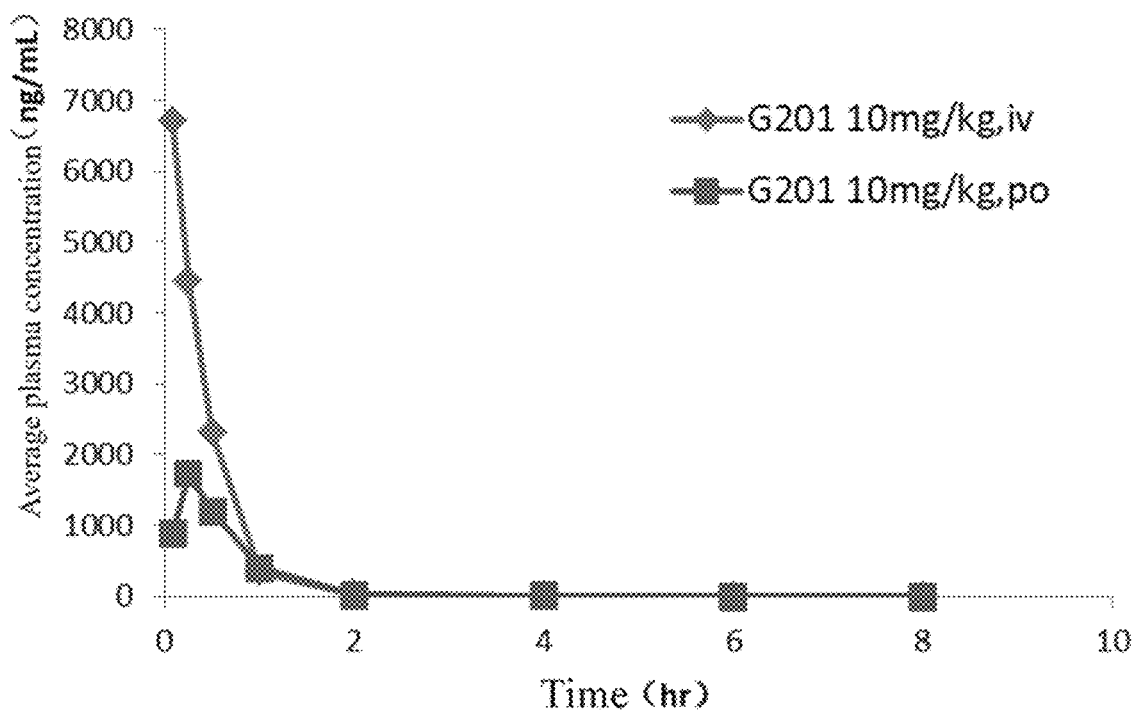
FIG. 3 shows a plasma concentration-time curve diagram of G201 intravenously injected and orally administered in ICR mice in Example 4 of the present invention.
Figure 4:
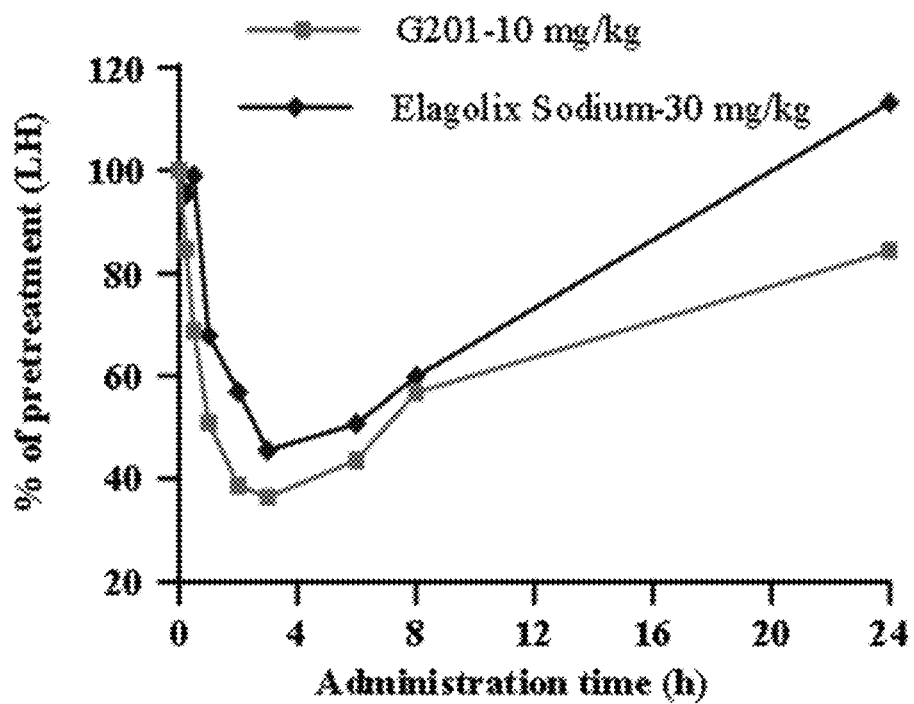
FIG. 4 shows a schematic diagram of the changing trend of serum LH in emasculated cynomolgus monkeys after oral administration of G201/Elagolix in Example 6 of the present invention (percentage value of LH relative to pre-administration, N=3).

The result showed that G201 intravenously administered in the mice had an average CL of 3.18 L/h/kg, an average $t_{1/2}$ of 0.26 h, and an average Vz of 1.17 L/kg. G201 was absorbed faster after oral administration to the mice, with $T_{max}$ of 0.27 h, average $AUC_{0-\infty}$ of 1,266.3 h*ng/mL, and absolute bioavailability of 38.9%, which was significantly higher than that of Elagolix (it was reported in a document that the absolute bioavailability of Elagolix in mice at a dose of 10 mg/kg was 10%). The plasma concentration-time curve for G201 intravenous and oral administration in the ICR mice was shown in FIG. 3, and pharmacokinetic parameters were shown in Table 2.

TABLE 2 pharmacokinetic parameters of G201 in ICR mice after oral and intravenous administration (mean value, n = 10)

| Parameter | Unit | Oral administration (10 mg/kg) | Intravenous injection (10 mg/kg) |
|---|---|---|---|
| $AUC_{0-t}$ | h*ng/mL | 1013.7 | 3239.9 |
| $AUC_{0-\infty}$ | h*ng/mL | 1266.3 | 3253.6 |
| $t_{1/2z}$ | h | 0.43 | 0.26 |
| $T_{max}$ | h | 0.27 | — |
| Vz | L/kg | — | 1.17 |
| CLz | L/h/kg | — | 3.18 |
| $C_{max}$ | ng/mL | 2004.2 | — |
| F | % | 38.9 | — |

Example 5

Plasma Protein Binding Assay:

Plasma of pre-incubated SD rats (5 males and 5 females) or healthy human plasma was taken and mixed thoroughly with working solutions, respectively, the working solutions contain different concentrations of the subjects (said subjects are G201 (1, 10, 100 μM) and Elagolix (10 μM)) and controls (warfarin sodium (10 μM)). After that, 50 μL of a drug-containing plasma sample was added to an equal volume of blank buffer as an unfiltered sample, and another 350 μ of drug-containing plasma sample was transferred into an ultrafiltration device (inner tube of ultrafiltration tube) for centrifugation (10000 g×3 min) at 37° C. After centrifugation, 50 μL of blank plasma was added to a sample removed from an outer tube (filtrate sample), and the same volume of blank buffer was added to a sample removed from the inner tube (filtered remaining sample). After mixing for 2 minutes, an internal standard solution was added. All the samples were vortexed for 10 minutes, proteins were precipitated by centrifugation, and supernatant was extracted. The concentrations of the subjects and controls were measured by an LC-MS/MS method. The free percentage (free percentage=(drug concentration of filtrate sample/drug concentration of unfiltered plasma)×100%) and the binging percentage (binging percentage=100%–free percentage) were calculated. Recovery (%)=(drug concentration of filtrate sample×volume+drug concentration of filtered remaining sample×volume)/drug concentration of unfiltered plasma×total volume× 100.

The results showed that the protein binding rates of Elagolix at 10 μM drug concentration with SD rat plasma and healthy human plasma were 87.71% and 87.25%, respectively, which were consistent with document reports.

The protein binding rates of G201 with SD rat plasma and healthy human plasma were 89.79% and 89.94%, respectively, which were slightly higher than those of Elagolix, and there was no drug concentration dependence in protein binding within a range of 1 to 100 μM.

TABLE 3 protein binding rates of G201 and Elagolix with rat and human plasmas

|  | SD rat plasma | | | Healthy human plasma | | |
| --- | --- | --- | --- | --- | --- | --- |
|  | G201 | Elagolix | Warfarin sodium | G201 | Elagolix | Warfarin sodium |
| Binding % | 89.79 | 87.71 | 99.08 | 89.94 | 87.25 | 98.76 |
| Free % | 10.21 | 12.29 | 0.92 | 10.06 | 12.75 | 1.24 |
| Recovery % | 102.54 | 106.44 | 95.36 | 99.23 | 96.98 | 113.78 |

Example 6

Pharmacodynamic Assay in Male Emasculated Cynomolgus Monkeys:

Three male cynomolgus monkeys (purchased from Guangxi GuiDong Quadrumana Development & Laboratory Co., Ltd.), 3 to 5 years old (weight 3.8 to 4.0 kg), were fasted overnight and underwent bilateral orchiectomy under anesthesia. Serum luteinizing hormone (LH) was measured in the cynomolgus monkeys from 3 to 7 weeks after emasculation using radioimmunoassay. The results showed that the serum LH in male cynomolgus monkeys increased significantly (about 10 folds) 3 weeks after emasculation until 7 weeks after emasculation when LH levels were basically stable.

After successful emasculation surgical modeling, G201 and Elagolix Sodium (dissolvent: 0.5% CMC-Na) were given in 2 administration cycles by single oral gavage at doses of 10 mg/kg and 30 mg/kg, respectively, both in a volume of 10 mL/kg. Each administration cycle was separated by an elution period of approximately 2 weeks. For each cycle of administration, blood was collected before and 0.25, 0.5, 1, 2, 3, 6, 8 and 24 h after administration, respectively, and serum was separated for gonadal hormone LH assay.

The results showed that serum LH decreased significantly after oral administration of G201 and Elagolix Sodium in emasculated cynomolgus monkeys, both reaching a minimum at 3 h after administration and then rising again. The serum LH in animals dosed at 30 mg/kg Elagolix Sodium returned to the pre-administration level at 24 h after administration. The serum LH in animals dosed at 10 mg/kg G201 has a slightly higher magnitude of change after administration than that in the animals dosed at 30 mg/kg Elagolix Sodium. During the assay period, all the animals were in generally good condition and had stable weights, and no subject-related abnormalities were observed.

As can be seen, G201 can significantly reduce serum LH levels in male emasculated cynomolgus monkeys by single oral administration, and its inhibitory effect at a dose of 10 mg/kg was already comparable or superior to that of Elagolix Sodium at a dose of 30 mg/kg.

To sum up, the present invention effectively overcomes the disadvantages in the prior art and has high industrial use value.

The above examples are merely illustrative of the principles of the present invention and its efficacy, and are not intended to limit the invention. Any of those skilled in the art may modify or change the above examples without departing from the spirit and scope of the present invention. Therefore, all equivalent modifications or changes made by those of ordinary skilled in the art without departing from the spirit and technical ideas disclosed in the present invention shall still be covered by the claims of the present invention.

What is claimed is:

1. A compound or a pharmaceutically acceptable salt, isomer, prodrug, polymorph or solvate thereof, a chemical structural formula of the compound is shown in Formula I:

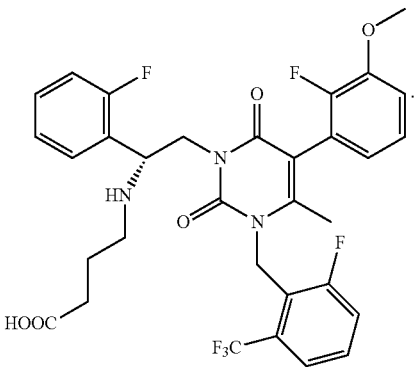

2. The compound or the pharmaceutically acceptable salt, isomer, prodrug, polymorph or solvate thereof according to claim 1, wherein the isomer is selected from a group consisting of an enantiomer, a diastereoisomer, a cis-trans isomer and a stereoisomer.

3. A preparation method for the compound according to claim 1, comprising: hydrolyzing a compound of Formula 1-12 to prepare and obtain the compound of Formula I, with the following reaction equation:

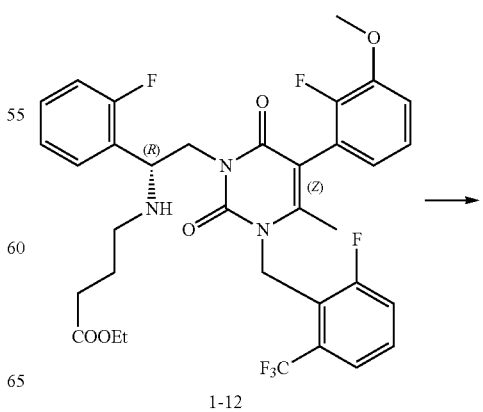

-continued

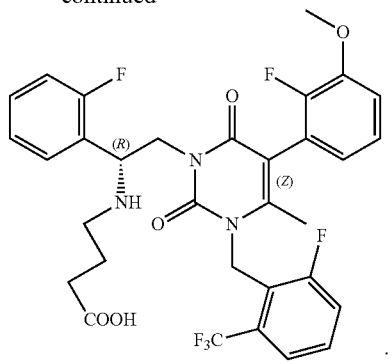

4. The preparation method according to claim 3, wherein the hydrolyzing is carried out in the presence of a base.

5. A method of preparing a drug for treating a gonadal hormone-related disease, comprising mixing the compound or the pharmaceutically acceptable salt, isomer, prodrug, polymorph or solvate thereof according to claim 1 with one or more pharmaceutically acceptable excipients.

6. The method according to claim 5, wherein the drug is a gonadotropin-releasing hormone receptor antagonist.

7. The method according to claim 5, wherein the gonadal hormone-related disease is selected from a group consisting of endometriosis, amenorrhea, menstrual irregularity, hysteromyoma, metrofibroma, polycystic ovarian disease, endometriosis, uterine leiomyoma, lupus erythematosus, hirsutism, precocious puberty, dwarfism, acne, alopecia, gonadotropin-dependent tumor, gonadotropin-producing pituitary adenomas, sleep apnea, irritable bowel syndrome, premenstrual syndrome, benign prostatic hyperplasia, contraception and infertility, and Alzheimer's disease.

8. The method according to claim 7, wherein the gonadotropin-dependent tumor is selected from a group consisting of prostate cancer, uterine cancer, breast cancer, ovarian cancer, and pituitary gonadotropic adenomas.

9. A drug composition, comprising the compound or the pharmaceutically acceptable salt, isomer, prodrug, polymorph or solvate thereof according to claim 1.

* * * * *